US00RE34753E

United States Patent [19]

Groiso

[11] E Patent Number: Re. 34,753

[45] Reissued Date of Patent: Oct. 4, 1994

[54] ORTHOPEDIC RIGID SPLINT-PLATE ORTHOSIS

[76] Inventor: Jorge A. Groiso, Ayacucho 1570 P.9, Buenos Aires 1112, Argentina

[21] Appl. No.: 737,405

[22] Filed: Jul. 29, 1991

Related U.S. Patent Documents

Reissue of:

[64] Patent No.: 4,852,556
Issued: Aug. 1, 1989
Appl. No.: 934,120
Filed: Nov. 24, 1986

[30] Foreign Application Priority Data

Sep. 26, 1986 [AR] Argentina ..... 305395

[51] Int. Cl.[5] ..... A61F 5/00

[52] U.S. Cl. ..... 602/7; 602/14; 602/22; 602/30

[58] Field of Search ..... 602/5, 6, 7, 12, 14, 602/20, 21, 23, 27, 28, 29, 30

[56] References Cited

U.S. PATENT DOCUMENTS

| | | | |
|---|---|---|---|
| Re, 30,541 | 3/1981 | Larson | 128/90 |
| 2,495,114 | 1/1950 | Leguillon et al. | 383/901 X |
| 3,176,685 | 4/1965 | Smarook | 128/90 |
| 3,494,726 | 2/1970 | Barasch | 206/438 X |
| 3,869,556 | 3/1975 | Rockland et al. | 426/634 |
| 4,006,741 | 2/1977 | Arluck | 128/90 |
| 4,165,817 | 8/1979 | Wengenroth et al. | 220/256 |
| 4,300,543 | 11/1981 | Rhee | 128/90 X |
| 4,323,586 | 4/1982 | Long | 383/101 X |
| 4,370,305 | 1/1983 | Affonso | 422/37 X |
| 4,486,488 | 12/1984 | Pietsch et al. | 128/155 X |
| 4,600,618 | 7/1986 | Raychok, Jr. et al. | 128/90 X |
| 4,661,535 | 4/1987 | Borroff et al. | 128/90 X |

FOREIGN PATENT DOCUMENTS

| | | | |
|---|---|---|---|
| 1456831 | 11/1976 | United Kingdom | 128/89 R |

*Primary Examiner*—Robert A. Hafer
*Assistant Examiner*—Brian E. Hanlon
*Attorney, Agent, or Firm*—Ostrolenk, Faber, Gerb & Soffen

[57] ABSTRACT

An orthopedic rigid splint-plate orthosis comprises a splint-plate which is provided in one of a combination of different shapes and sizes corresponding to different body members which may have to be treated. The splint-plate has at one of its edges a non-stretchable linking ribbon which at the end thereof opposite to the end joined to the plate includes locking means which are complementary with corresponding locking means provided in the edge of the plate opposite to that edge joined with the ribbon. The plate is provided presterilized and isolated inside an impervious bag which may be filled with boiling water to make the rigid splint-plate soft, whereafter the water is drained and the softened plate applied and moulded to the body member and then left to harden back to its rigid state. For use in an operating theatre, the bag with the plate may be closed inside a second bag and sterilized with gas or radiation; thereafter, the plate may be softened by submerging the sealed outside bag in hot water.

11 Claims, 3 Drawing Sheets

ORTHOPEDIC RIGID SPLINT-PLATE ORTHOSIS

Matter enclosed in heavy brackets [ ] appears in the original patent but forms no part of this reissue specification; matter printed in italics indicates the additions made by reissue.

BACKGROUND OF THE INVENTION

1. Field of the invention

The present invention relates to an orthopedic rigid bandage-plate orthosis or splint useful for medical applications, especially those applications in which some parts of the human body have to be secured against movement during a predetermined therapeutic treatment period. This includes treatment for foot deviations such as various foot, metatarsus aductus, overlapping toes, pes talus and bunions; sprained and fractured fingers and toes; sprained ankles; trigger finger; post-operative immobilization for neck, foot and hand surgery; genu valgum; torticollis; scoliosis; thoracic trauma; and provisional immobilization. Other uses may be those related to aesthetic and plastic surgery, and those in the veterinary field.

2. Description of prior art

Splints made of plastic-like materials are well-known in the art. One kind of splint is provided in rigid form and has to be moistened in water in order to be softened and wound around the human body member to be protected.

Another kind of rigid orthosis comprises a thermoplastic material plate provided in the form of a large sheet, from which each splint has to be cut in the proper shape according to the injured human body member. Once cut, the plastic rigid splint must be perforated and binding ribbons riveted thereto. It is then sufficiently heated in a skillet, pan or other adequate means to transform the thermoplastic [materialito] *material into* a soft state, whereafter the orthosis may be duly applied to and wrapped around the pertinent body member. Thereafter, the ribbons are wound around the splint and tied using a special adhesive to keep the splint in place until it cools and reverts to its normal rigid state.

In emergency situations, the time and expertise necessary to cut the rigid bandage-plate in the proper shape and the need to prepare it represent important drawbacks. If trained personnel for cutting this plate happen to be unavailable, when the emergency situation arises, it is very probable that incorrectly cut splints may be obtained.

Another drawback of the prior art method and means is due to the investment and cost of obtaining and keeping the large sheet material from which the relatively small plates are cut from time to time. Furthermore, there are left-overs from the cut material which constitute significant wastes thereof.

Other drawbacks and disadvantages result from the initial lack of sterilization of the thermoplastic sheet and the need of significant accessories such as the skillet or pan, stove or heater, drill, riveter, special adhesive, etc. The initial lack of sterilization may be dangerous if the cut plate is not heated sufficiently, e.g. when the water is warmed but not boiled, and furthermore, is inadmissable in operating theatres. In fact, when sterilization is needed, an additional step is required using gas or radiation for sterilizing the splint.

These drawbacks generally limit the availability and use of these splints to hospitals and clinics and preclude widespread storage and use in private consulting-rooms.

BRIEF SUMMARY OF THE INVENTION

Therefore, an object of the present invention is to provide orthosis means which may be bought individually, costing a fraction of the investment required by prior art means.

Another object of the present invention is to provide orthosis means which may be applied without the need of accessory means, i.e. skillet, heater, tools or separate ribbons and adhesive.

Another object of the present invention is to provide orthosis means which eliminate the waste of leftovers.

Another object of the present invention is to provide orthosis means which drastically reduce the time and expertise necessary for preparing the splint, such that it may be swiftly applied by the doctor himself.

Another object of the present invention is to provide orthosis means which may be widely available and used in any type of medical establishment, large or small, including private consulating rooms.

Another object of the present invention is to provide orthosis means which are assuredly sterilized.

Another object of the present invention is to provide orthosis means which may be easily and safely used in operating theatres.

In order to overcome the above cited drawbacks and to realize said objects, the present invention provides orthopedic rigid splint-plate orthoses which are particularly adapted to different human body parts which may have to be therapeutically treated, such that each splint-plate may form a rigid protection which can be directly moulded on the skin of the patient without any risk of burning thereof. The splint-plate is made of thermoplastic material, the composition and thermoplastic characteristics of which are well-known in the art. See for example U.S. Pat. No. 4,600,618 issued Jul. 15, 1986. The rigid splint-plate is provided within a bag made of a plastic material having good resistance to hot water. The splint is provided in the bag, said splint having already been cut in a specific shape and size, with at least one fixing strip or ribbon attached at one edge of the splint. The free end of the strip has locking means which match complementary locking means on the opposite edge of the splint or on the free end of a second strip attached thereto.

The splints of the present invention are provided in the bags, said splints having already been sterilized the bags, and are made available in different shapes and sizes, such that an individual practitioner need only stock a small quantity of easily storable splint packets.

When needed, a bagged splint of the proper size is taken from the cupboard or appropriate storage means, and subjected to a heating operation while still inside the bag, so that the state of the splint-plate is changed from rigid to soft. Thereafter, the thence soft splint-plate is removed from the bag and moulded by hand on the body part to be treated. Then the ribbon is wrapped around the soft splint to keep it in place until it has hardened.

Consequently, in emergency situations, the rigid splint of the present invention is immediately available and easily usable and, therefore, the patients run no risks due to time-delays and lack of personnel. The rigid splints, in accordance with the present invention, will have the correct shape for the corresponding human body part, since they will be manufactured and precut by dedicated personnel skilled in this art. The advantages of this are that the proper splint will be simply selected and correctly located for the pertinent human body part, even by non-skilled personnel, due to its predetermined correct shape, and thus leftovers are eliminated. Sterilization of the splint is optional, and *it* should only taken out of the bag once it has been heated to its soft state. The [split] *splint* is thus isolated from contamination during storage time, which may be quite long in small establishments. Furthermore, all contact with preparation tools is eliminated, as is the need for special accessories to prepare the splint. Sterilization is optional; in fact, an individual physician may simply use hot water from his coffee maker to heat the splint prior to application, since boiling water is indeed not necessary if the splint is just to be softened.

According to a preferred embodiment, the present invention provides orthopedic splint-plate, orthoses, each comprising a thermoplastic material splint-plate having a shape corresponding to the body member to be treated, the plate having at one of its edge a linking strip or ribbon made from a non-stretchable material joined thereto at one of its ends. At its opposite end, the linking strip includes locking means complementary with locking means provided on the plate, at an edge opposite to said one edge of the plate joined to the strip. The rigid plate is provided isolated in an impervious material bag which is aseptically closed, which bag is mechanically resistant to the weight of the splint-plate as well as thermally resistant to the temperature of hot water up to and including boiling point. Prior to application, the bag is cut open at one end and hot fluid poured in to soften the splintplate. Once the thermoplastic plate is soft, the heating fluid is emptied and the plate is removed from the bag. Thenceforth, the plate is ready to be applied to a body.

Alternatively, to ultimately preserve sterilization of the splint, the closed bag may be submerged in hot fluid to soften the plate inside and opened only for removal of the then-softened plate. For post-surgery use in an operating theatre, the original sealed bag with the plate inside may be placed inside an additional bag which is sealably closed and subjected to radiation or gas for sterilizing it and its contents.

In addition, the rigid splint-plate orthosis of the present invention may be provided with a foam padded surface which is intended to be in contact with the skin of the patient. The foam pad may be of thermoplastic material. The plate may be gridded with holes to facilitate skin breathing as well as saving material and providing a lighter splint.

The present invention further features a method for immobilizing an injured body member part during a treatment period, which method comprises the steps of providing a rigid splint-plate comprised of thermoplastic material and thermally resistant bag means containing said splint-plate, the thermoplastic splint-plate having complementary fastening means located at opposite sides thereof, subjecting said plate to a hot fluid to heat and relatively soften it whilst still inside the bag means, removing the softened splint-plate from said bag means and said hot fluid, applying said soft splint-plate to at least a part of said injured body member and manually moulding it to substantially conform to the shape of said body member part, locking the soft splint-plate plate in place with said fastening means and waiting for said thermoplastic splint-plate to revert to its rigid state, whereby said rigid splint-plate firmly grips and immobilizes said injured body member part.

BRIEF DESCRIPTION OF THE DRAWINGS

In the several Figures, the same reference numerals indicate the same parts of the rigid splint-plate orthosis.

DETAILED DESCRIPTION OF PREFERRED EMBODIMENTS

Figure 1:
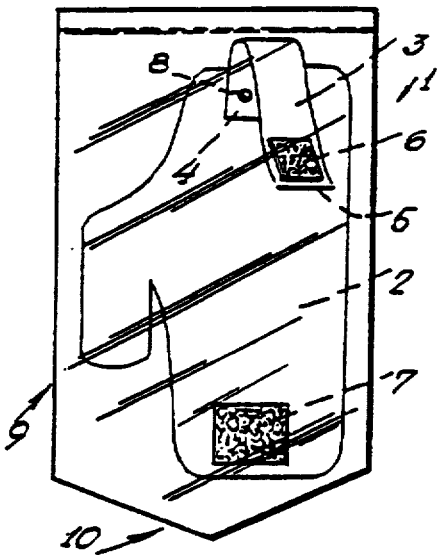
FIG. 1 is a perspective general view of the rigid splint-plate orthosis of the invention, wherein the splint-plate is located within a bag ready for sale.
Figure 2:
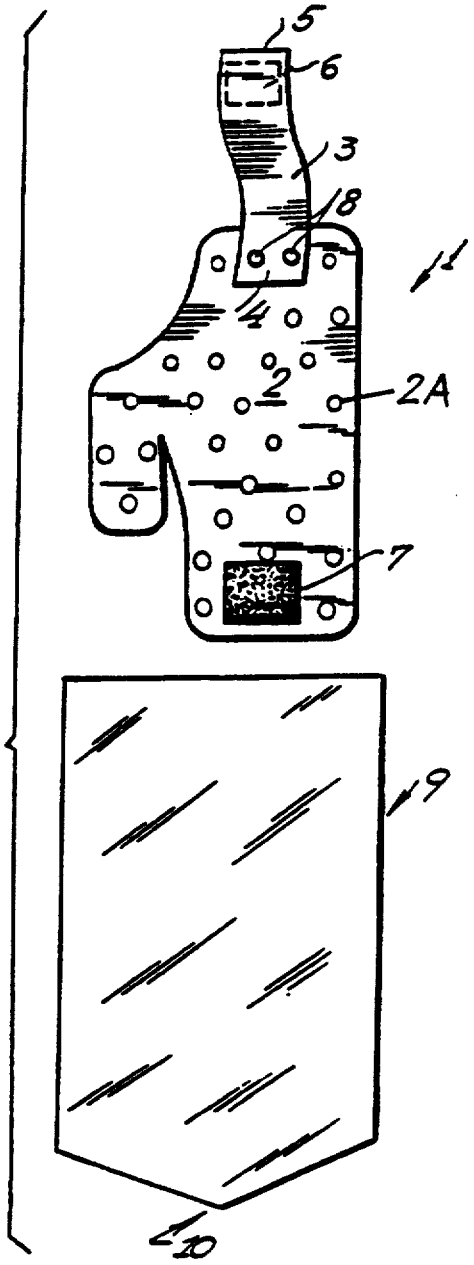
FIG. 2 shows the bag of FIG. 1 with the rigid splint-plate removed therefrom.

Consider first FIGS. 1 and 2. Reference numeral 1 generally indicates the orthopedic rigid splint-plate orthosis of the invention consisting of a thermoplastic splint-plate 2, which in accordance with a particular use has one of several shapes and sizes, and a bag 9 which is made from an impervious material.

Splint-plate 2 includes a ribbon or strip 3, which is made from a non-stretchable and thermally resistant material. The strip 3 is joined, at one of its ends 4, to the splint-plate 2, by means of any suitable joining means 8, such as a pair of stainless rivets. The other end 5 of the strip 3 includes locking means 6 which are complementary with corresponding locking means 7 located in the splintplate 2. The locking means 6 and 7 may be of any suitable nature, such as typical hook and loop means. In any case, the locking means 6, 7 and the joining means 8 must be capable of firmly retaining the splint-plate around the body member of the patient, at least until the plate 2 is rigid.

As stated above, the splint-plate 2 is originally provided and stored within the bag 9 to keep it sterilized. This bag 9 may be made from a plastic material, laminar or not, but, in any case, the bag must be capable of resisting the weight of the splint-plate 2 as well as the temperature of hot water, which is poured inside the bag 9 or in which the bag is submerged, in order to cause the plate 2 to adopt a soft state. Preferbly, the bag 9 has a pentagonal-like shape, in order to define a tip 10 which may be cut to allow discharge of the water after heating. Obviously, the bag 9 may have any other kind of configuration which allows discharge of the water upon requirement. In any case, the splint-plate [orthesis] *orthosis/*and bag 9 will preferably be aseptic in its interior.

When preparing the orthopedic rigid splint-plate orthosis 1 of the present invention for use, the physician, assistant or less skilled operator cuts the upper part of the bag 9 and pours the boiling water inside the bag 9. He then waits between one and two minutes to let the splint-plate 2 warm into a soft state. Once the splint-plate 2 is soft, the end 10 of the bag 9 is cut to function like a funnel allowing the discharge of the hot water. When practically all the water is discharged, the necessary part of the bag will be cut in order to permit removal of the splint-plate 2, which may then be placed directly over the skin of the patient in the region to be treated.

Figure 4:
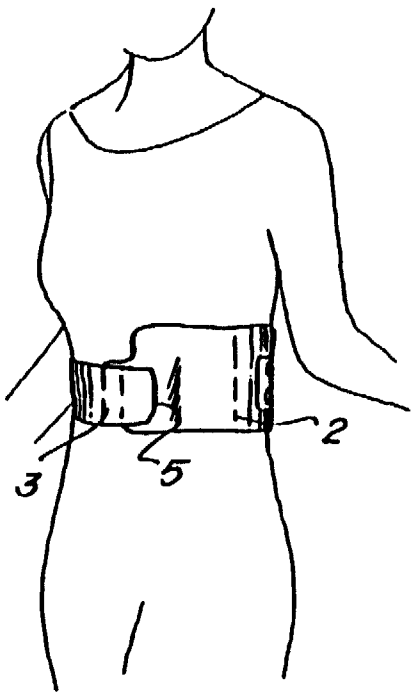
FIGS. 4 shows another way, from among many other possibilities, of using the orthosis of the present invention.
Figure 3A:
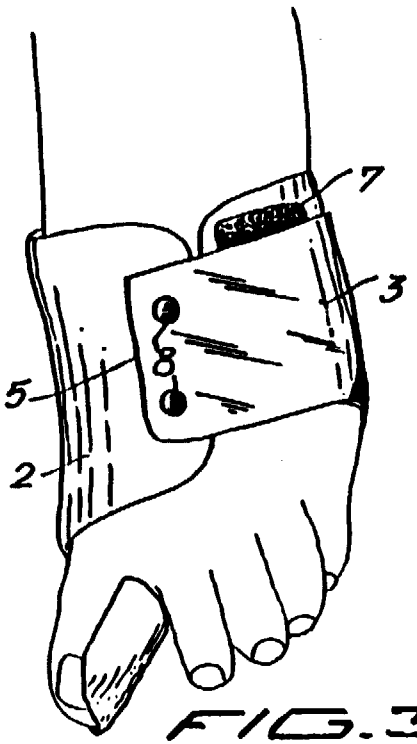
FIG. 3A shows the splint of FIG. 3 applied, for example, to correct a bunion.
Figure 3:
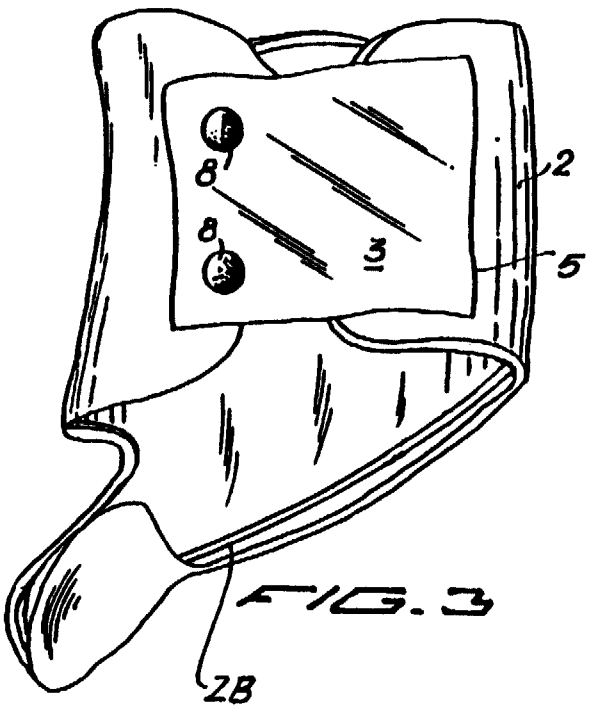
FIG. 3 illustrates the definite shape of the splint of FIGS. 1 and 2, once moulded, wrapped around and fastened to an (unillustrated) body member.

The necessary shape of the splint-plate, as illustrated in FIGS. 3, 3A and 4, is obtained by pressing with the fingers on the soft plate 2. Once the plate 2 is cooled, it reverts back to its original rigid state, where it will grip itself around the member of the patient and the strip 3 will perform an accessory fastening function. An adhesive strip may be used for the strip 3. The entire preparation and casting operation takes only a few minutes or so and requires no special instrumentation nor hardly any skill.

Another important feature of the present orthosis is that, during the therapeutic period or treatment, any necessary zone of the plate 2 may be reheated and remoulded on the body of the patient, in order to correct the position of the splint 2, as well as to relieve any excess pressure exerted in such zones.

Figure 5:
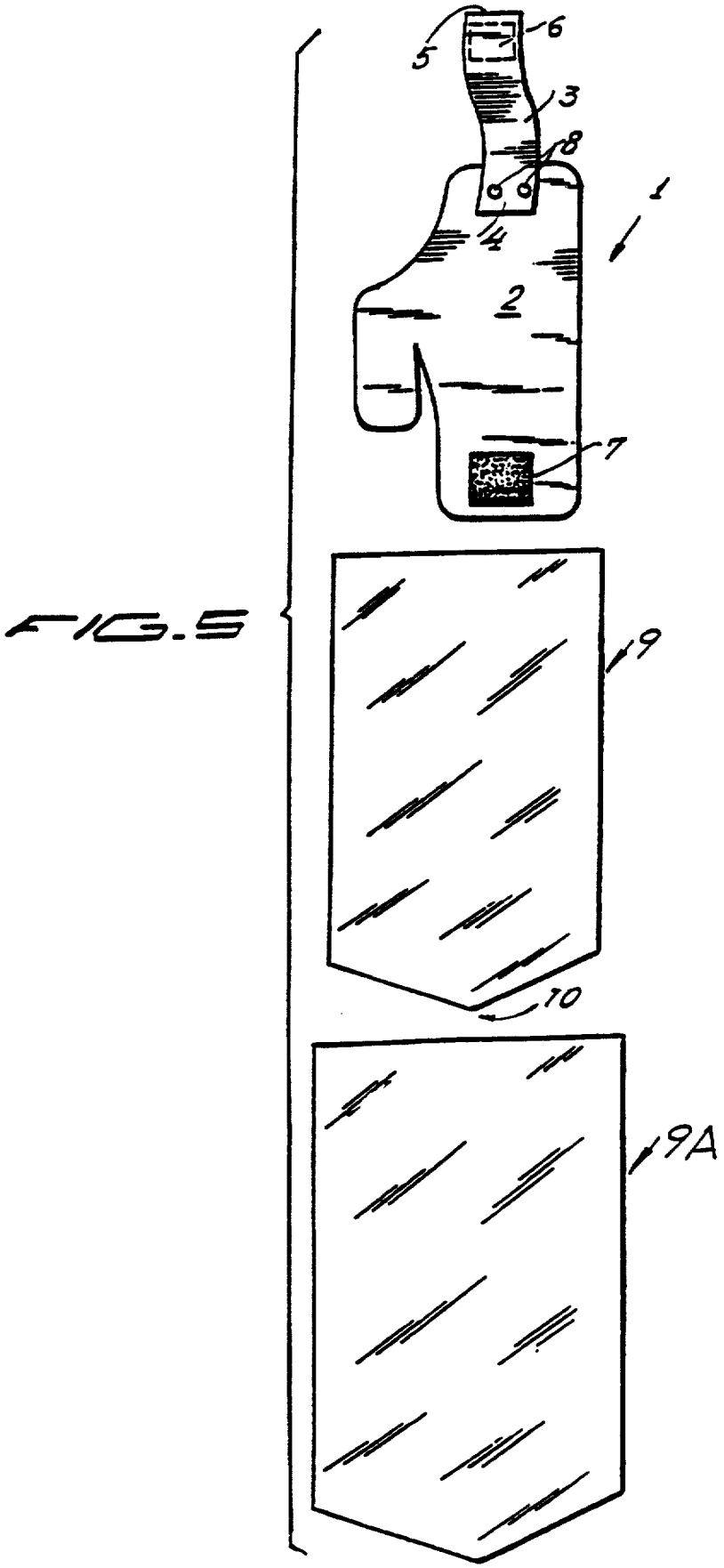
*FIG. 5 shows the invention having a second bag.*

The use of the present invention in an operating theatre differs somewhat, insofar that initially the sealed bag 9 is enclosed in a second [(not illustrated)] *9A shown in FIG. 5*, which is sealed and sprayed with ethylene oxide gas. The molecular apertures of the plastic material used for the bags, e.g., nylon ar large enough for the gas molecules to pass through and too small for the microbes; hence, all contents of the bags are effectively sterilized until the bag is opened. Of course, other forms of gas or radiation may be employed. When needed, the pair of closed bags is submerged in hot water and, once the plate 2 has softened, the circulating nurse cuts open the outside bag and the scrub nurse then opens the inside bag 9. Into neither of the two bags is hot water poured.

Another feature of the rigid splint-plate 2 of the present invention is that the splint-plate 2 may be lined with a foam pad [(not illustrated)] *2B* on an inner face thereof, which lined face is intended to be in contact with the skin of the patient. This pad surface is intended to avoid hurting the skin of the patient, as well as to make the rigid splint 2 more comfortable. This pad surface may be perforated and may comprise a thermoplastic material. *Also, the plate may be gridded with holes 2A to facilitate skin breathing as well as saving material and providing a lighter splint.*

Although the essential features of the invention have been brought out by means of a preferred embodiment, the invention is not limited to this embodiment and extends on the contrary to all alternative forms within the purview of the appended claims.

I claim:

1. A method for immobilizing an injured body member comprising:

(a) opening [the] *a* bag in a combination comprising a splint-plate *and the bag, with the splint plate* inside [a water] *the bag, the bag being liquid* impervious, aseptically closed [bag], mechanically resistant to the weight of the splint-plate and thermally resistant to temperatures at or below the boiling point of water, the splint-plate comprising a rigid thermoplastic plate pre-cut to conform to a specific body member [and provided with fastening means attached thereon];

(b) pouring a liquid into the opened bag, the liquid being at a temperature at or below the boiling point of water and above the softening point of the thermoplastic splint plate;

(c) allowing the splint-plate to remain in the liquid until the splint-plate softens;

(d) removing the softened splint-plate from the bag;

(e) applying the softened splint-plate to a body member and molding it to fit the body member; and (f) securing the splint-plate in place around the body member [with the fastening means].

2. The method according to claim 1, wherein the softened splint-plate is removed from the bag by cutting the bottom of the bag to allow the liquid to drain from the bag.

3. The method according to claim 1, wherein the splint-plate is secured in place using at least one non-stretchable linking strip, one end of the strip being connected to the splint-plate and the other end of the strip being provided with a locking means which is engageable with a complementary locking means attached to the splint-plate.

*4. The method according to claim 1, wherein the step of securing comprises securing the splint-plate in place around the body member with a fastening means attached to the splint-plate.*

*5. A combination for immobilizing an injured body member comprising an orthopedic splint-plate, a liquid-impervious, aseptically closed bag holding the splint-plate, the bag being mechanically resistant to the weight of the splint-plate and thermally resistant to temperatures at or below the boiling point of water, said bag being provided for receiving a hot liquid therein at or below the boiling point of water thereby to soften the splint-plate, the splint-plate comprising a rigid thermoplastic plate pre-cut to conform to a specific body member, the thermoplastic plate being deformable to conform to the body member after heating to a temperature at or below the boiling point of water, and becoming rigid on the body member upon subsequent cooling, said splint-plate further comprising a plurality of holes therethrough which permit the circulation of air from one face of the splint-plate to its other face.*

*6. The combination according to claim 5, further comprising fastening means attached to the thermoplastic plate for securing the plate to the body member.*

*7. The combination according to claim 5, wherein the bag has a V-shaped bottom part which can easily be cut to discharge the contents of the bag.*

*8. The combination according to claim 6, wherein the fastening means comprises at least one non-stretchable locking strip, one end of the strip being provided with a locking means which is engageable with a complementary locking means attached to the splint-plate.*

*9. The combination according to claim 5, wherein the splint-plate has a face intended to contact the body member comprising padding.*

*10. A combination for immobilizing an injured body member comprising an orthopedic splint-plate, a liquid-impervious, aseptically closed first bag holding the splint-plate, the bag being mechanically resistant to the weight of the splint-plate and thermally resistant to temperatures at or below the boiling point of water, the splint-plate comprising a rigid thermoplastic plate pre-cut to conform to a body member and being deformable to conform to the body member after being heated in the bag to a temperature at or below the boiling point of water and becoming rigid on the body member upon subsequent cooling, and further comprising a second bag disposed about and sealing the first bag so that the second bag containing the first bag with the splint-plate may be submerged in a hot liquid to soften the splint-plate without contact of the hot liquid with said first bag and splint plate, said bags being permeable to sterilizing gas for sterilizing the splint-plate, but impermeable to the hot liquid and to microbes.*

*11. A combination for immobilizing an injured body member comprising an orthopedic splint-plate, a liquid-impervious, aseptically closed bag holding the splint-plate, the bag being mechanically resistant to the weight of the splint-plate and thermally resistant to temperatures at or below the boiling point of water, the splint-plate comprising a rigid thermoplastic plate pre-cut to conform to a body member, the thermoplastic plate being deformable to conform to the body member after being heated in the bag to a temperature at or below the boiling point of water and becoming rigid on the body member upon subsequent cooling, said bag being permeable to sterilizing gas for sterilizing the splint-plate, but impermeable to hot liquid and to microbes.*

* * * * *